United States Patent [19]

Nickson et al.

[11] Patent Number: 4,745,219

[45] Date of Patent: May 17, 1988

[54] CHEMICAL INTERMEDIATES AND A PROCESS FOR THEIR PREPARATION

[75] Inventors: Thomas E. Nickson, St. Charles; John P. Chupp, Kirkwood; Thomas E. Neumann, Creve Coeur, all of Mo.

[73] Assignee: Monsanto Company, St. Louis, Mo.

[21] Appl. No.: 894,540

[22] Filed: Aug. 8, 1986

Related U.S. Application Data

[63] Continuation of Ser. No. 552,886, Nov. 17, 1983, abandoned.

[51] Int. Cl.$^4$ .................. C07C 102/00; C07C 103/34; C07C 79/10
[52] U.S. Cl. .................................... 564/146; 564/218; 568/936; 568/937
[58] Field of Search ................ 564/146, 218; 568/936, 568/937

[56] References Cited

U.S. PATENT DOCUMENTS

| | | | |
|---|---|---|---|
| 892,900 | 7/1908 | Schraube et al. | 564/146 X |
| 2,406,578 | 8/1946 | Bart | 564/146 |
| 2,459,002 | 1/1949 | Parker et al. | 564/146 X |
| 3,111,403 | 11/1963 | Soper | 564/146 X |
| 3,442,945 | 5/1969 | Olin | 564/146 X |
| 4,036,838 | 7/1977 | Vogel et al. | 564/146 X |

*Primary Examiner*—Paul F. Shaver
*Attorney, Agent, or Firm*—Robert B. Martin

[57] ABSTRACT

This invention pertains to chemical intermediates for a new class of 2-haloacetanilide herbicides and a process for preparation of these intermediates. The process generally involves nitration of substituted benzotrifluoride compounds.

5 Claims, No Drawings

CHEMICAL INTERMEDIATES AND A PROCESS FOR THEIR PREPARATION

This is a continuation of application Ser. No. 552,886 filed Nov. 17, 1983, now abandoned.

FIELD OF THE INVENTION

The invention herein pertains to chemical intermediates and a process for the preparation of these intermediates. The chemical intermediates are useful for the preparation of a substituted aniline which is a precursor for a new class of 2-haloacetanilide herbicides.

BACKGROUND OF THE INVENTION

It has recently been discovered that a certain class of 2-haloacetanilide herbicides are particularly useful in safely controlling hard-to-kill perennial weeds such as quackgrass, nutsedges and many others in the presence of a variety of crops including cotton, corn, and soybean. This new class of herbicides is described and claimed in Belgium Patent 887,997 issued September 18, 1981. A particularly effective herbicide within this class is N-(ethoxymethyl)-2'-(trifluoromethyl)-6'-methyl-2-chloroacetanilide.

The present invention relates to chemical intermediates in the production of compounds within this new class of herbicides. The present invention also relates to a process for preparing these chemical intermediates. This process generally involves nitration of substituted benzotrifluoride compounds.

Electrophilic substitution such as nitration, sulfonation, etc. of various types of substituted benzene compounds is known in the art. It is also known that substituents on the benzene ring can affect both the reactivity and orientation of electrophilic substitution. Certain substituents can increase the reactivity of the benzene ring by donating electron density to the ring inductively or by resonance. Other groups withdraw electron density from the ring and thus reduce the reactivity of the ring.

Ring substituents can either direct electrophilic substitution at the ortho, para, or meta positions. With a plurality of substituents, the substituents can either reinforce or oppose each others directive influence. Activating substituents generally prevail over deactivating substituents. Generally, electrophilic substitution onto a benzene ring having a plurality of substituents which individually direct substitution at alternative open positions on the ring will result in a mixture of substitution products.

It is an object of the present invention to provide new intermediate compounds useful in the production of compounds within a new class of 2-haloacetanilide herbicides.

It is another object of this invention to provide a process for preparing some of these new intermediate compounds.

It is another object of this invention to provide a new aromatic nitration directing system.

Other objects and advantages will become apparent from the following disclosure.

SUMMARY OF THE INVENTION

The present invention relates to certain chemical intermediate compounds and a process for making these compounds. The novel intermediate compounds are useful in the production of a substituted aniline which is a precursor for the preparation of compounds within a new class of 2-haloacetanilide herbicides.

The novel intermediate compounds of this invention are 2-nitro-3-methyl-5-chloro-6-$C_{1-4}$ alkylamidobenzotrifluoride and 2-nitro-3-methyl-5,6-dichlorobenzotrifluoride. $C_{1-4}$ alkylamido radical is ROCNH radical where R is $C_{1-4}$ alkyl.

The process of the present invention generally involves nitration of the corresponding un-nitrated precursor benzotrifluoride compound to form the nitrated intermediate compound.

A starting compound which can be used in the preparation of the intermediate compounds of the present invention is the known compound 3-methylbenzotrifluoride.

The 3-methylbenzotrifluoride can be nitrated with a suitable nitrating agent to form a mixture of nitration products including the 6-nitro isomer. The 6-nitro compound can be isolated and reduced by standard laboratory procedures to obtain 3-methyl-6-aminobenzotrifluoride. The 3-methyl-6-aminobenzotrifluoride can be chlorinated using standard laboratory procedures to give 3-methyl-5-chloro-6-aminobenzotrifluoride. This compound can then be converted into either of the corresponding un-nitrated precursor benzotrifluoride compounds, 3-methyl-5-chloro-6-$C_{1-4}$ alkylamidobenzotrifluoride or 3-methyl-5-chloro-6-chlorobenzotrifluoride, by acetylation or the Sandmeyer reaction respectively, using standard laboratory procedures. The un-nitrated precursor benzotrifluoride compounds are then nitrated with a suitable nitration agent in accordance with the process of the present invention to form the intermediate compounds of the present invention.

Using standard laboratory procedures, the intermediate compounds of the present invention can be converted into the precursor aniline, 2-methyl-6-trifluoromethylaniline. This precursor aniline can then be converted into 2-haloacetanilides within this new class of herbicides according to known procedures. A more thorough disclosure of the present invention is presented in the detailed description which follows.

DETAILED DESCRIPTION OF THE INVENTION

The present invention relates to intermediate compounds and the process for their preparation. These intermediate compounds are useful in the preparation of an aniline which is a precursor for compounds within a new class of 2-haloacetanilide herbicides. The novel intermediate compounds of the present invention are (a) 2-nitro-3-methyl-5-chloro-6-$C_{1-4}$ alkylamidobenzotrifluoride (1trifluoromethyl-2-nitro-3-methyl-5-chloro-6-$C_{1-4}$ alkylamidobenzene) (herein referred to as NAB) and (b) 2-nitro-3-methyl-5,6-dichlorobenzotrifluoride (1-trifluoromethyl-2-nitro-3methyl-5,6-dichlorobenzene) herein referred to as NCB). The novel intermediate compounds have the following formula:

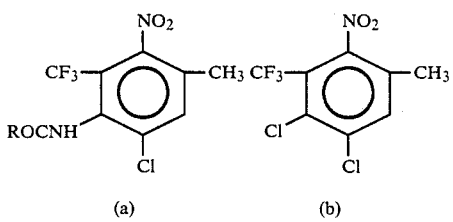

wherein R is $C_{1-4}$ alkyl.

The process of the present invention generally involves nitration of the corresponding un-nitrated precursor benzotrifluoride compound with a suitable nitrating agent as follows:

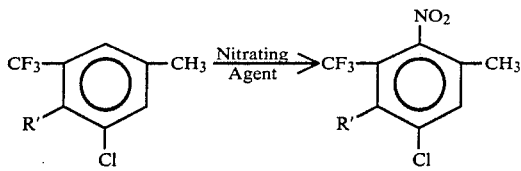

wherein R' is chloro or $C_{1-4}$ alkylamido.

A starting compound which can be used in the preparation of the intermediate compounds of the present invention is 3-methylbenzotrifluoride. The 3-methylbenzotrifluoride can be prepared in accordance with the procedures set forth in the chemical literature: J.A.C.S. 65 389 (1943) and Chem Letters 1719 (1981). The 3-methylbenzotrifluoride can also be prepared by reduction by standard laboratory procedures of commercially available 3-chloromethyl benzotrifluoride or 3-trifluoromethyl benzaldehyde or 3dichloromethyl benzotrifluoride prepared in accordance with U.S. Pat. No. 4,367,348 or J. Org. Chem. 43 1071 (1978).

The 3-methylbenzotrifluoride is then nitrated with a suitable nitrating agent such as nitric acid or oxides of nitrogen, e.g. dinitrogen pentoxide. Conveniently a molar excess of nitric acid can be utilized. Other acids such as sulfuric acid can be used as a cosolvent to maintain a concentrated acid solution during the course of the reaction. It has been found that the presence of sulfuric acid may, in some cases, result in the formation of greater amounts of the 6-nitro isomer as a nitration product. Conveniently the nitration reaction is run at a temperature from about $-10°$ C. to about 60° C. After the mononitration reaction is complete, the nitration products can be recovered by phase separation. The predominant products of the mononitration reaction are the 2- and 6-nitro isomers. The 2-nitro isomer can be separated and reduced by standard laboratory techniques to form the precursor aniline. The 6-nitro isomer can also be separated from the mixture by standard laboratory techniques. The nitration reaction generally results in the formation of about 35% of the 6-nitro isomer.

The 6-nitro compound can then be reduced by standard laboratory techniques to form 3-methyl-6-aminobenzotrifluoride. Conveniently the 6-nitro compound is dissolved in a suitable polar solvent such as methanol and hydrogenated with hydrogen gas and a suitable hydrogenation catalyst such as palladium.

The 3-methyl-6-aminobenzotrifluoride can be chlorinated by standard laboratory techniques to form 3-methyl-5-chloro-6-aminobenzotrifluoride. Conveniently, the benzotrifluoride is dissolved in a suitable solvent, such as carbon tetrachloride, at a low temperature, e.g. $-20°$ C., and a slight molar excess of a suitable chlorinating agent, such as t-butylhypochlorite, is slowly added to the mixture. Lower temperatures may result in a slightly larger yield and higher temperatures may result in over chlorination. Chlorination is completed in a short period of time, e.g. ½ hour, and the product isolated by standard laboratory techniques. The benzotrifluoride can also be chlorinated at room temperature with about 1.1 equivalents of N-chlorosuccinimide in a suitable solvent, such as acetonitrile.

The 3-methyl-5-chloro-6-aminobenzotrifluoride can be converted into the un-nitrated precursor to NAB, 3-methyl-5-chloro-6-$C_{1-4}$ alkylamidobenzotrifluoride by acetylation using standard laboratory procedures. The benzotrifluoride is conveniently dissolved in a suitable organic solvent, such as acetic acid, ethylene dichloride or dichloromethane. The mixture is heated to about 40° C. to about 80° C. and a slight molar excess of an anhydride, such as acetic anhydride, or an acid chloride, such as acetylchloride, is added with stirring. The mixture is then stirred for a couple of hours to form the un-nitrated precursor to NAB which is isolated by standard laboratory techniques.

The 3-methyl-5-chloro-6-aminobenzotrifluoride can also be converted into the un-nitrated precursor to NCB, 3-methyl-5,6-dichlorobenzotrifluoride, utilizing the known Sandmeyer reaction. Conveniently the benzotrifluoride is slurried into a six normal solution of hydrochloric acid containing about one equivalent of sodium nitrite. This mixture is then added slowly to a solution of concentrated hydrochloric acid containing about 0.5 equivalents of cuprous chloride. The mixture is then heated to about 70° C. for a short period of time to form the un-nitrated precursor to NCB which is isolated by standard laboratory techniques.

The novel nitrated intermediates, NAB and NCB, of the present invention are then formed in accordance with the process of the present invention by nitrating the corresponding un-nitrated precursor with a suitable nitrating agent such as nitric acid, oxides of nitrogen, e.g. dinitrogen pentoxide or nitronium tetrafluoroborate. The precursors are preferably purified by standard laboratory techniques prior to nitrating to avoid the formation of other nitration products. The nitration can be conveniently accomplished using concentrated nitric acid or a mixture of concentrated nitric acid and a suitable acid cosolvent, e.g. pleum, sulfuric acid, phosphoric acid. Prior to nitrating the precursor to NAB, it is preferred to first mix the precursor with a suitable acid cosolvent, e.g. sulfuric acid. If desired the precursor to NCB may also be mixed with an acid cosolvent prior to nitration. Conveniently a molar excess of about 2 to about 10, e.g. about 7.0 of concentrated sulfuric acid, e.g. about 96%, is mixed with the precursor. The sulfuric acid functions both as a solvent for the nitration reaction and an agent to sequester water formed during the reaction. During the mixing with sulfuric acid, the reaction medium is conveniently cooled to control the exotherm.

After addition of precursor to the acid cosolvent, the precursor is nitrated. Conveniently the nitration agent comprises a mixture of concentrated nitric acid and concentrated sulfuric acid. The nitration agent is slowly added to the reaction mixture while the temperature is maintained at about $-10°$ C. to 70° C., preferably about 10° to 60° C. For each mole of precursor, the nitration mixture conveniently comprises about 1 to about 2, e.g. 1.2 molar equivalents of 98% nitric acid and about 2 to about 20, e.g. 7 molar equivalents of 96% sulfuric acid. After the addition of the nitrating agent, the mixture is stirred for about ½ to about 3 hours. Longer stirring times may reduce the yield. The mixture is then cooled, conveniently by pouring over ice, and the nitration product extracted with a suitable organic solvent, such as ethyl acetate. The nitration product may be isolated from the reaction mixture using standard laboratory procedures, such as fractional crystallization. The nitration of each precursor generally results surprisingly in the formation of greater than 90% yield of the 2-nitro isomer without any readily detectable formation of any other nitro isomers.

The novel intermediate NAB of the present invention can be converted into the precursor aniline, 2-methyl-6-trifluoromethylaniline, by deacetylation, deamination via the diazonium salt and reduction using standard laboratory procedures. Deacetylation can be conveniently accomplished by dissolving NAB in a suitable polar solvent, such as alcohol or water, preferably ethanol, and reacting it with about 0.1 to about 6 molar equivalents of concentrated sulfuric acid at a temperature of about 25° C. to 65° C. The deacetylated product may then be conveniently isolated by neutralizing the reaction mixture with a suitable base, such as sodium hydroxide, and solvent extracting the product with a suitable inert organic solvent, such as ethyl acetate.

Reductive deamination is conveniently accomplished by reacting the deacetylated product with aqueous sulfuric acid and aqueous sodium nitrite. The resulting diazonium salt can be reduced with ethanol and metallic copper using standard laboratory techniques.

Reduction to hydrodehalogenate the ring and reduce the nitro group may be accomplished using standard laboratory procedures. The deaminated product is conveniently dissolved in a solution of a suitable HCl scavenger, such as trimethylamine and a polar solvent, such as alcohol. A suitable hydrogenation catalyst is added to the solution, such as palladium on carbon. Hydrogenation is accomplished with about 2.7-3.4 atmospheres hydrogen gas. The deacetylation, deamination and reduction of the intermediate NAB results in the formation of the precursor aniline.

The novel intermediate NCB of the present invention can be converted into the precursor aniline, 2-methyl-6-trifluoromethylaniline, by hydrogenation using standard laboratory procedures to reduce the nitro group and hydrodehalogenate the ring. NCB is conveniently dissolved in a solution of suitable HCl scavenger, such as triethylamine and a polar solvent, such as an alcohol. A suitable hydrogenation catalyst is added to the solution, such as palladium on carbon. Hydrogenation is accomplished with about 2.7-3.4 atmospheres of hydrogen gas.

The precursor aniline may then be converted into compounds within the class of tertiary 2-haloacetanilide herbicides by a variety of methods. For example, the tertiary 2-haloacetanilides may be prepared by haloacetylation of the precursor aniline by known procedures to form a secondary 2-haloacetanilide which is then N-alkylated to form compounds within the new class of tertiary 2-haloacetanilide herbicides. The haloacetylation of the precursor aniline can be accomplished by adding a slight molar excess of chloroacetyl chloride to the aniline in a suitable organic solvent, such as toluene, and heating the solution to reflux for a short period of time. The secondary 2-haloacetanilide is then N-alkylated according to known procedures to form the tertiary 2-haloacetanilide herbicides.

A suitable N-alkylation process is described in detail in U.S. Pat. No. 4,258,196. A modified N-alkylation process is described in U.S. Pat. No. 4,284,564. The tertiary 2-haloacetanilides may also be made by a transetherification process. This process is described in U.S. Pat. No. 4,296,254. The tertiary 2-haloacetanilide can also be prepared from the precursor aniline by the procedure set forth in Belgium patent No. 887,997. These patents are incorporated herein by reference.

The following examples are presented to illustrate the present invention as well as some of the various embodiments of the invention. These examples are presented as being illustrative of the novel process of the invention and are not intended to be a limitation as to the scope thereof.

EXAMPLE I

Preparation of NAB 2.5 gms of 3-methyl-5-chloro-6-acetamidobenzotrifluoride was added to 7 mls of cold 96% sulfuric acid with stirring. A small exotherm was observed. The mixture was cooled to about 0° C. and 3 ml of a solution comprising 1 ml of 90% nitric acid and 2 mls of 96% sulfuric acid was added dropwise with stirring. After the addition, the mixture was stirred for 1 hour while maintaining the temperature at 0° C. The temperature was allowed to rise to room temperature and the mixture stirred for about 1 more hour. The mixture was poured over ice, filtered and dried. Yield 2.8 gms (93.3% yield) of white solid m.p. 203°-205° C. (decomposes).

EXAMPLE II

Preparation of NCB

At 0° C., 1.5 gms of oleum (1.2 m moles of SO$_3$) was slowly added to 3 gms (47.6 m moles) of 98% nitric acid. 2.3 gms of 3-methyl-5,6-dichlorobenzotrifluoride was added to the acid mixture at 0° C. After the addition, the mixture was allowed to warm up to room temperature and stirred for about ½ hour. The mixture was poured over ice water, extracted with ethyl acetate, dried, filtered and concentrated on rotary evaporator to give 2.6 gms of a yellow colored solid (96.3% yield) m.p. 45°-47° C.

Although this invention has been described with respect to specific embodiments, the details hereof are not to be construed as limitations, for it will be apparent that various equivalents, changes and modifications may be resorted to without departing from the spirit and scope thereof and it is understood that such equivalent embodiments are intended to be included within the scope of this invention.

We claim:

1. A process for preparing the compound having the formula:

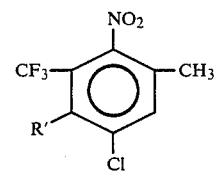

which comprises nitrating the compound having the formula:

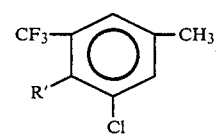

wherein the above formula R' is chloro or $C_{1-4}$ alkylamido radical.

2. The process of claim 1 wherein the Compound II is nitrated with nitric acid.

3. The process of claim 1 wherein the Compound II is nitrated with a mixture of nitric acid and sulfuric acid.

4. The process of claim 1 wherein the process is carried out at a temperature of about 10°–60° C..

5. The process of claim 1 wherein the Compound II is nitrated with a mixture comprising about 1.0 to about 2.0 molar equivalents of concentrated nitric acid and about 2.0 to about 20 molar equivalents of concentrated sulfuric acid.

* * * * *